United States Patent [19]

Shippert

[11] Patent Number: 5,507,807
[45] Date of Patent: Apr. 16, 1996

[54] APPARATUS FOR THE RELEASE OF A SUBSTANCE WITHIN A PATIENT

[76] Inventor: Ronald D. Shippert, 4975 S. Albion St., Littleton, Colo. 80121

[21] Appl. No.: 204,528

[22] Filed: Mar. 1, 1994

[51] Int. Cl.$^6$ .................................................. A61F 2/12
[52] U.S. Cl. ........................... 623/8; 623/11; 623/17; 604/64; 604/59; 604/181
[58] Field of Search ............................. 623/8, 11, 17, 623/20; 604/57, 59, 60, 64, 181

[56] References Cited

U.S. PATENT DOCUMENTS

| | | | |
|---|---|---|---|
| 2,647,512 | 8/1953 | Johnson | 604/64 |
| 4,471,765 | 9/1984 | Strauss et al. | 604/181 |
| 4,474,308 | 10/1984 | Bergeron | 604/59 |
| 4,955,906 | 9/1990 | Coggins et al. | 623/8 |
| 5,201,779 | 4/1993 | Shiao | 623/8 |
| 5,304,119 | 4/1994 | Balaban et al. | 604/64 |
| 5,336,163 | 8/1994 | DeMane et al. | 606/192 |

*Primary Examiner*—Paul B. Prebilic
*Attorney, Agent, or Firm*—Sheridan Ross & McIntosh

[57] ABSTRACT

An applicator is disclosed for injecting or releasing a fluidic or solid substance into a cavity or tissue of a patient. The applicator is used to release a contained substance along the length of the applicator when the applicator has been inserted and positioned in the patient. Thus, if required, the substance to be released can easily be dispensed along a particular path such that a proper amount of the substance is dispensed along the path. In particular, the applicator of the present invention is useful in placing absorptive foam pads within a nasal cavity and in inserting implants into a breast.

18 Claims, 6 Drawing Sheets

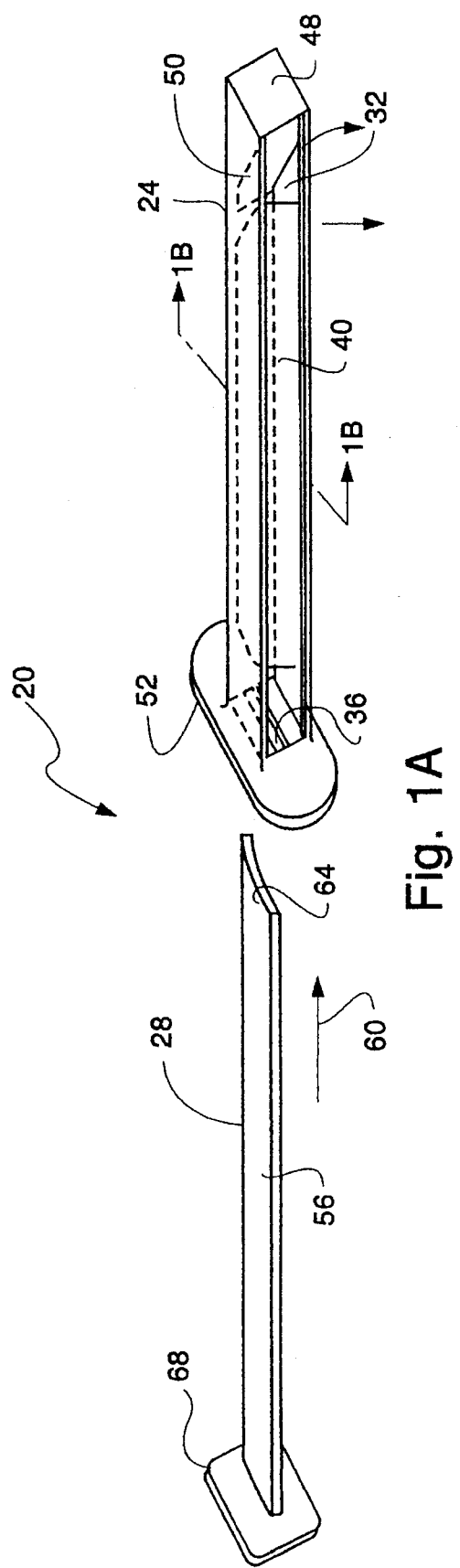
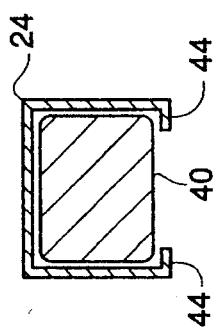
Fig. 1A
Fig. 1B

APPARATUS FOR THE RELEASE OF A SUBSTANCE WITHIN A PATIENT

FIELD OF THE INVENTION

The present invention relates to a device for releasing a substance into a cavity or tissue of a patient. In particular, an injection or insertion device is disclosed for this purpose.

BACKGROUND OF THE INVENTION

There are numerous medical devices for inserting or injecting a substance into tissue or a body cavity. Such devices typically have an opening for releasing the substance into a body area substantially at the end of the device which first enters the body such as a conventional hypodermic needle when used for injections. Thus, the substance is released into the body area substantially about this first entry end of the device. Further, the substance is released generally in a flow in-line or parallel with the longitudinal axis of the body insertion portion of the device.

Such medical devices or applicators as described above have disadvantages which make them awkward to use in certain contexts. For example, if the substance to be dispensed into a body area must be positioned along a particular path, the applicator user is required to position the opening for releasing the contained substance concurrently and/or iteratively with the releasing of the substance. Further, the amount of the substance released at any time must also be controlled.

Therefore, it would be advantageous to have an applicator that is able to release a substance into a body area without the above mentioned disadvantages. In particular, it would be advantageous to have an applicator which, once positioned, is able to release a substance into a body area along a predetermined path without requiring repositioning and/or without requiring a user to exercise substantial control over the amount of the substance released along the path.

SUMMARY OF THE INVENTION

The present invention is an applicator for releasing a substance into a body area along a predetermined path wherein, once the applicator is positioned for substance dispensal, the substance is released from the applicator without requiring further repositioning and without the need for a user to exercise substantial control in dispensing an appropriate amount of the substance along the path. In particular, the applicator of the present invention releases the substance for dispensal along a length of the applicator inserted into a body area instead of at an applicator end as in conventional applicators. In a preferred embodiment, the applicator of the present invention releases the substance in one or more directions substantially perpendicular to the length of the applicator. That is, the dispensed substance is released from a housing chamber provided along the length of the applicator such that the substance is dispensed through one or more openings along the length thereby dispensing an appropriate amount of the substance into the body area adjacent and along an inserted length of the applicator.

In a first embodiment, the applicator of the present invention includes a housing having retaining rails about the one or more dispensal openings along the length of the applicator. The retaining rails restrict the opening(s) sufficiently to retain a solid substance, such as an absorptive foam pad, within the housing chamber until the applicator is properly positioned for dispensing the substance within a body area. Once positioned, the solid substance is urged out of the housing chamber opening(s) by a plunger incorporated into the applicator of the present invention.

In a second embodiment of the applicator of the present invention, the applicator includes a slidable panel which assists in containing the substance to be dispensed such that the substance remains within the housing chamber until the applicator is properly positioned. Once positioned, the slidable panel is retracted from a closed position (inhibiting substance release) to a fully retracted position, thereby permitting the contained, potentially fluidic, substance to contact an adjacent body area. Note that the substance may thereby flow from the housing chamber under the influence of gravity or be urged out of the chamber housing by a plunger included in the applicator.

Thus, it is an aspect of the present invention to release a substance into a body area such that the release is along a length of the applicator.

It is a further aspect of the present invention that it can be used for release of a substance within various body areas, including body cavities as well as intra-tissue areas.

It is a further aspect of the present invention to release the substance in a direction substantially different from a direction which is tangent to the length of the applicator at the distal end where the applicator is first inserted into a body area.

It is a further aspect of the present invention to provide a simpler method to dispense a substance along a path within a body area.

It is a further aspect of the present invention to release either a substantially fluidic substance or a solid substance into a body area.

It is a further aspect of the present invention that the length of the housing chamber may be curved in a predetermined manner for proper positioning within a body area.

It is yet a further aspect of the present invention that the housing may be flexible so as to permit proper positioning within a body area.

It is a further aspect of the present invention that it can be customized in terms of size and shape to accommodate a particular insertion body area, insertion procedure and substance to be released.

Other features and benefits of the present invention will become apparent from the detailed description, together with the accompanying figures included hereinafter.

BRIEF DESCRIPTION OF THE DRAWINGS

FIGS. 1A and 1B present a first embodiment of the applicator of the present invention whereby this embodiment is useful for releasing a solid substance 40 into a body area. In particular, FIG. 1A presents an exploded, oblique view of the applicator and FIG. 1B presents a cross-section of the applicator housing 24;

DETAILED DESCRIPTION

Figure 2:
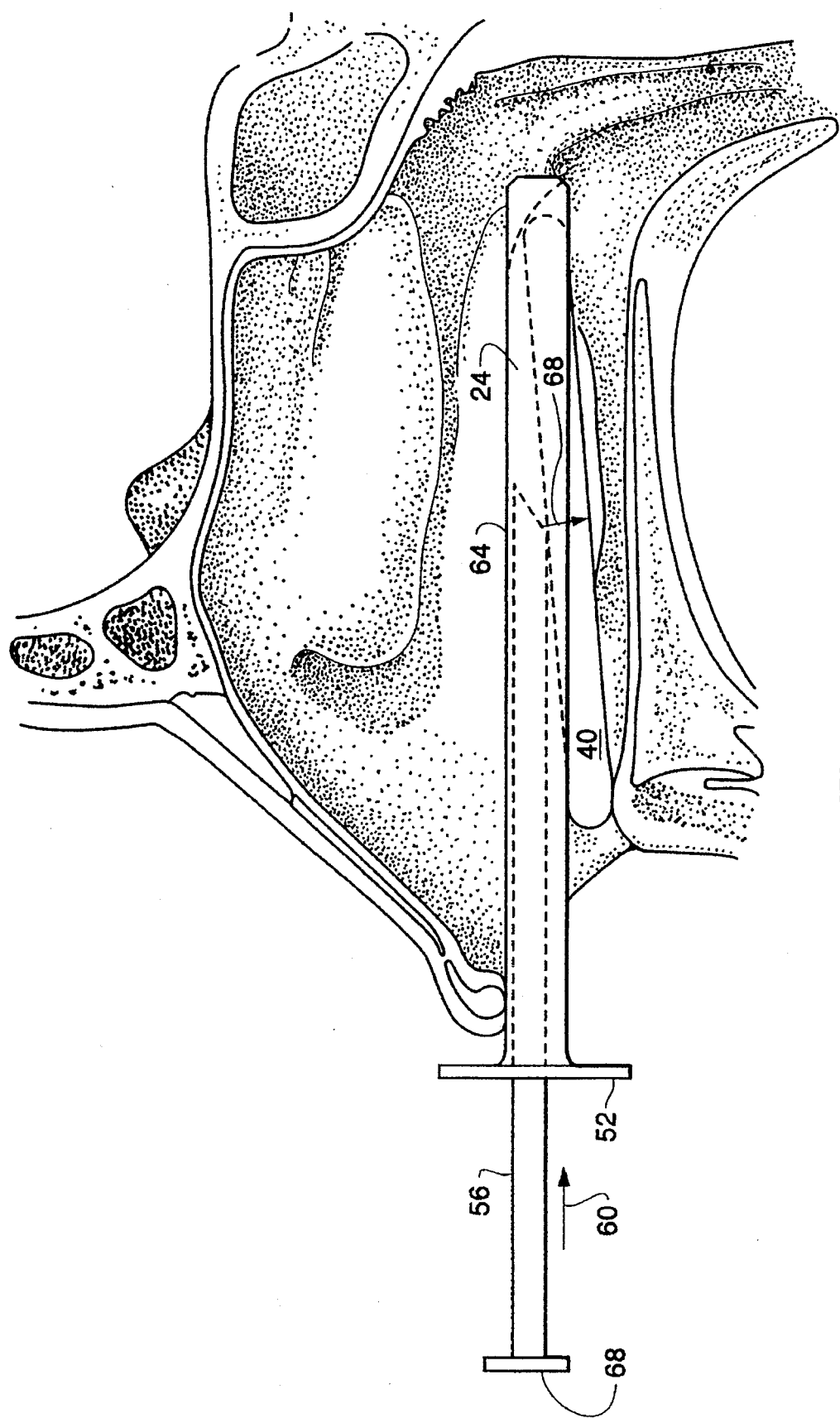
FIG. 2 illustrates the operation of the embodiment of the present invention shown in FIGS. 1A and 1B. In particular, the applicator is shown in the process of releasing an absorptive foam pad 40 within the nasal cavity of a patient.

In FIGS. 1A and 1B, a first embodiment of the applicator 20 of the present invention is presented. This embodiment 20 consists of a housing 24 for storing a substance to be released into a body area and a plunger 28 which is insertable into a chamber 32 within the housing via a chamber opening 36. The chamber 32 provides the storage area for a solid substance 40 which is to be released from the housing 40 into a body area. As can be seen best in FIG. 1B, the solid substance 40 is held within the chamber 32 by rails 44 which restrict the opening to the chamber 32 and thereby retain the solid substance 40 when no countervailing forces are applied to it. Referring again to FIG. 1A, the rails 44 run substantially the length of the housing 24. That is, the rails 44 run from a closed distal end 48 of the housing 24, having a curved chamber end 50, to the opposite end of the housing which is integrally attached to a gripping wing 52. Note that the gripping wing 52 extends outwardly beyond this opposite end of the housing 24 in order that a user of the applicator 20 can grip or hold the gripping wing 52 with his/her fingers during applicator 20 use.

Referring now to the plunger 28, the plunger includes a shaft 56 having a length along the direction 60 that is substantially the length of the chamber 32 also along direction 60. In general, it is preferred that the length of the plunger 28 be at least greater than one-half the length of the chamber 32. At the end of the shaft 56, which is insertably received into the chamber opening 36, is a foot or substance contact wedge 64 that is used for forcibly releasing the solid substance 40 from the chamber 32 when the shaft is urged in the direction 60. At the opposite end of the shaft 56 from the foot 64 is a plunger handle 68 by which a user may apply force in the direction 60 to release the substance 40 from the chamber 32.

FIG. 2 presents an illustration of the operation of the applicator 20 in the context of applying a foam absorptive pad 40 within the nasal cavity of a patient. Note that as the plunger foot 64 is urged in the direction 60, the absorptive pad 40 is urged out of the applicator 20 in a direction 68 which is substantially different from the direction along the length of the housing 24 (i.e., direction 60). In particular, the direction 68 is substantially orthogonal to the housing length. Further note that when the foot 64 contacts the curved chamber end, their interactions are such that the end of the absorptive pad 40 adjacent to the curved chamber end 50 is urged completely free of the applicator 20. Thus, once the absorptive pad 40 is completely released from the applicator 20, the applicator can then be withdrawn from the nasal cavity leaving the absorptive pad 40 properly positioned.

Figure 3:
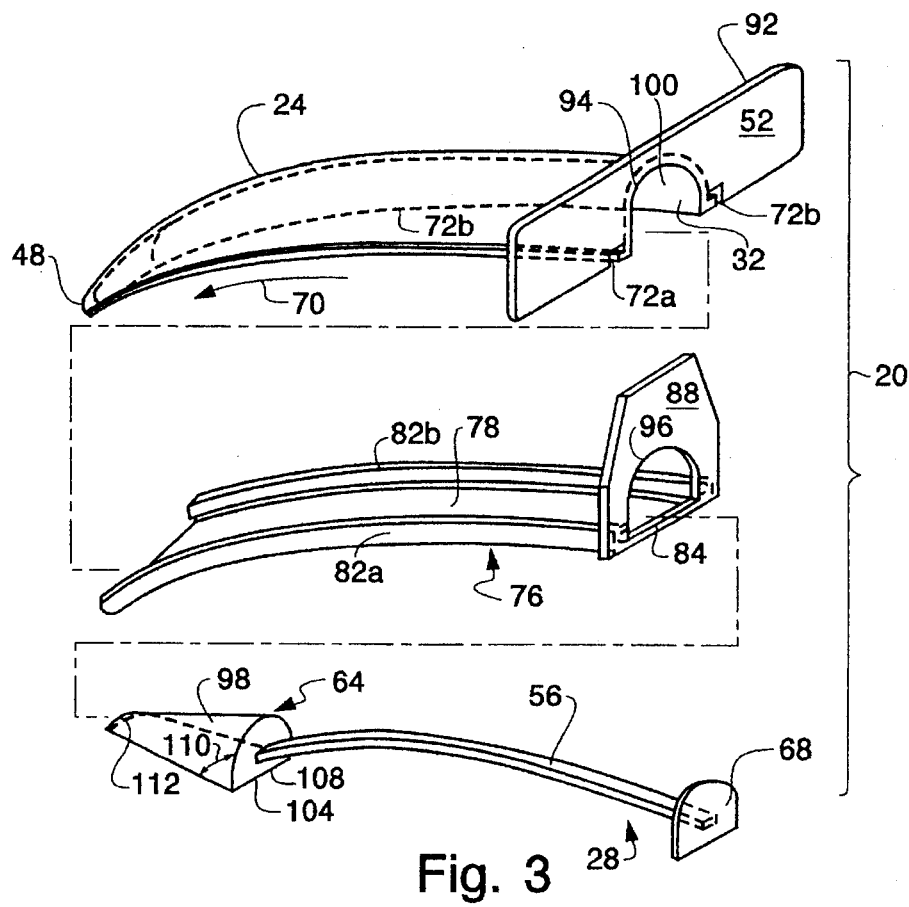
FIG. 3 presents an exploded view of the components of a second embodiment of the applicator of the present invention.
Figure 6:
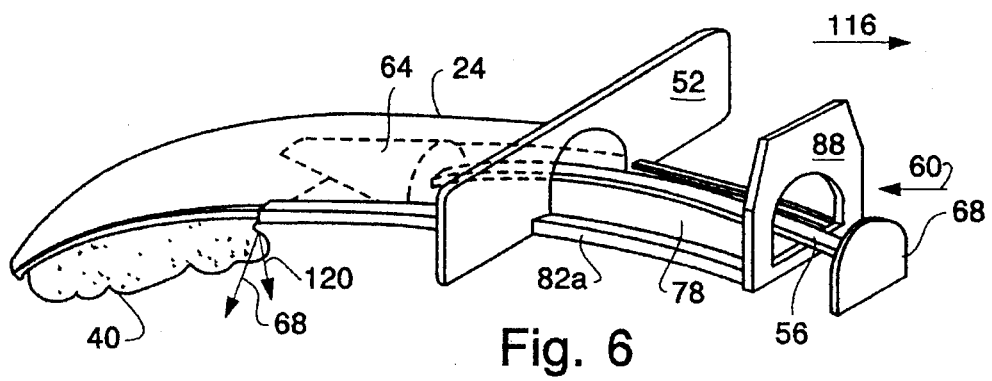
FIG. 6 illustrates an alternative method for releasing a substance 40 into a breast area using a substantially straight version of the second embodiment of the applicator.

In FIG. 3, second embodiment of the applicator 20 is presented. In describing this embodiment, components which are functionally equivalent to those in the first embodiment of FIGS. 1A and 1B have been given the same labels. In FIG. 3, note that for substantially the length of the housing 24 (i.e., along curve 70), each cross-section is substantially round. In general, the cross-section of the housing 24 can have any one of a plurality of shapes, including elliptical, oval and rectangular. Further note that, in this embodiment, the distal end 48 of the housing 24 is tapered to provide easier insertion into a body area. Also note that the length of the housing 24 is also curved to parallel arc 70, thereby allowing the housing to conform more closely to a body area within which the housing is to be inserted. Moreover, the housing 24 may be made of materials which are substantially flexible, thus increasing the capability of the applicator 20 to conform to the contour of a body area. Along the parallel edges running the length of the chamber 32 are parallel tracks 72a and 72b. The tracks 72 are used to attach a substance retaining assembly 76 to the housing 24 such that a potentially fluidic substance 40 can be retained in the chamber 32 substantially by the substance retaining assembly 76 closing the chamber opening running the length of the housing 24 between the tracks 72. To accomplish this, the substance retaining assembly 76 includes a panel member 78 for covering the lengthwise opening of chamber 32. In addition, the substance retaining assembly 76 also includes parallel in-turned runners 82a and 82b which extend the length of the panel member 78, although it should be understood that the runners could be turned outwardly. During operation of the applicator 20, the track 72a is slidably received in the space between runner 82a and the panel member 78, while the track 72b is slidably received in the space between the runner 82b and the panel member 78. Note that the substance retaining member 76 may also be composed of a flexible material which facilitates ease of assembly with the housing 24 and flexibility in conforming to an inserted body area.

Attached to the substance retaining assembly end 84 is a tab 88 projecting substantially perpendicular to the surface of the panel member 78. When the runners 82 are fully engaged with the tracks 72, the tab 88 is adjacent to the gripping wing 52 on the side opposite the chamber 32. Further, the tab 88 extends upwardly beyond the gripping wing edge 92 such that the tab 88 provides an easily accessible portion that can be used for sliding the runners 82 along the tracks 72 when engaging or disengaging the substance retaining assembly 76 from the housing 24.

A plunger 28 for the present embodiment of the applicator 20 is also presented. The shaft 56 of the plunger has opposing ends attached to a foot 64 and a handle 68. Note that the housing 24 and the substance retaining assembly 76 each has rear openings 94 and 96, respectively, through which foot 64 passes during assembly of the applicator 20. The foot 64 has an upper surface 96 which matches or conforms to an interior chamber surface 100 which is substantially uniform in shape throughout the length of the chamber 32. Thus, upon assembly and operation of the applicator 20 of this embodiment, the upper surface 98 and the chamber surface 100 maintain a sufficiently tight fit with one another so that a substance 40 being released into a body area may not flow between the upper surface 96 and the chamber surface 100. In addition, the foot 64 also includes a lower surface 104 which extends from a foot base edge 108 upwardly at an acute angle 110 to a foot apex 112. The foot apex 112 can have a shape which allows this portion of the foot 64 to slide within the reduced cross-sectional portion of the chamber 32 near the distal end 48. Thus, during use of this embodiment of the applicator 20, the lower surface 104 contacts the substance 40 within the chamber 32 while the foot base edge 108 maintains a sufficiently tight fit with the panel member 78 so that the substance 40 may not flow between them. Also note that at least the shaft 56 of the plunger 28 may be composed of a flexible material such that the foot 64 can easily slide within the volume enclosed between the housing 24 and substance retaining member 76.

The operation of the present embodiment of the applicator 20 will now be discussed with reference to FIGS. 4–7. In particular, in FIG. 4, the applicator 20 has been assembled and the chamber 32 has been filled with a potentially fluidic substance 40 for release into a body area. Thus, the substance retaining assembly 76 fully encloses the substance 40 within the chamber 32 with the exception of the rear opening 94 of the housing 24, this opening being plugged by the foot 64 of the plunger 28.

Figure 4:
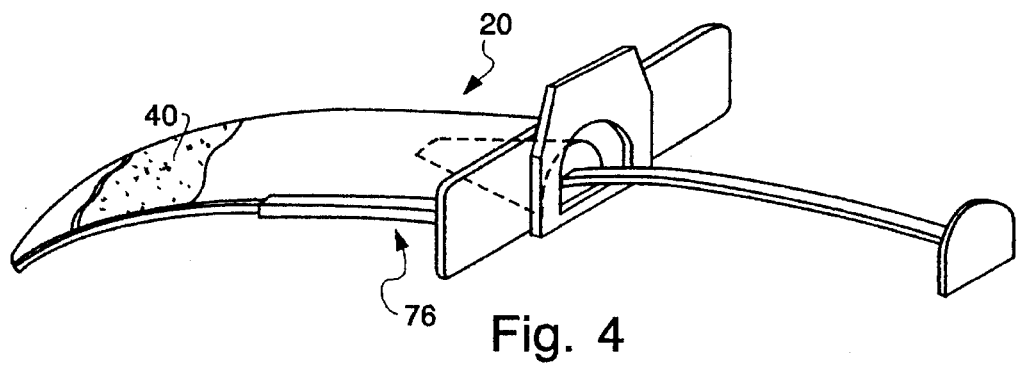
FIG. 4 presents an assembled oblique view of the second embodiment of the applicator as it appears when a substance 40, to be released within a body area, is contained within the housing chamber 32 as would be the case during the insertion of the applicator into a body area.
Figure 5:
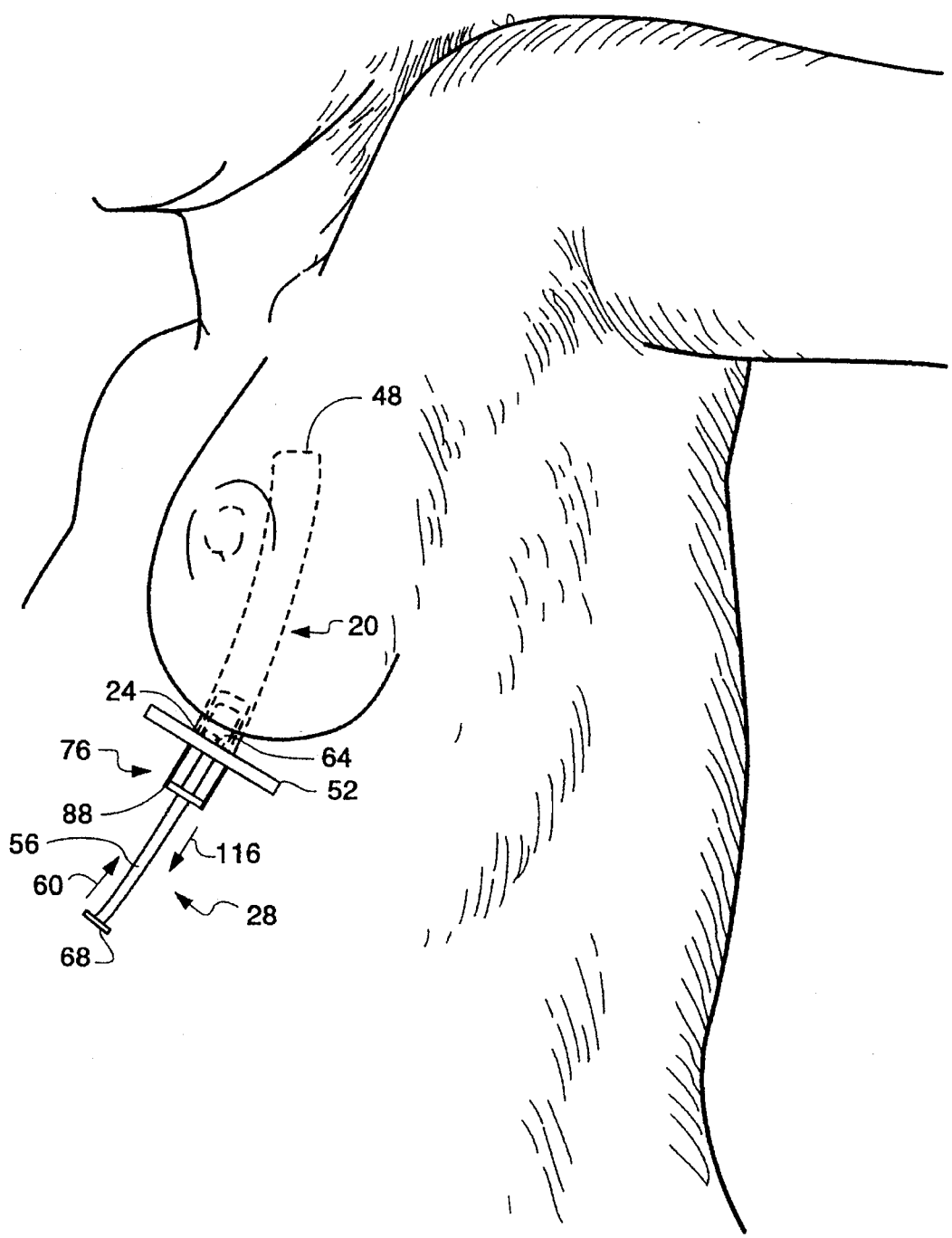
FIG. 5 illustrates the use of the second embodiment of the applicator for releasing a substance 40, such as an implant, into a breast area of a patient.

In FIG. 5, the present embodiment of the applicator 20 is shown positioned with a curved housing 24 substantially within a breast area whereby the release of a substance 40 within the breast is commencing. As an aside, note that it is preferable for an applicator 20 used in inserting breast implants to have a housing 24 of sufficient length such that it can substantially span a diameter of the breast along the insertion path. Thus, once the applicator 20, as configured in FIG. 4, is positioned in the breast area substantially as, for example, in FIG. 5, the substance retaining assembly 76 may be retracted in the direction of arrow 116 thereby allowing substance 40 to come in contact with adjacent breast area tissue. Concurrent with or subsequent to the retraction of substance retaining assembly 76, a user of the applicator 20 can exert force on handle 68 in the direction of arrow 60, thus urging the substance 40 through the opening created by the retraction of substance retaining assembly 76. In this context, it is worth noting that by substantially fully retracting the substance retaining assembly 76 prior to exerting force on handle 68 in the direction 60, a substantially uniform amount or dosage of the substance 40 can be released along the path of the inserted portion of the housing 24 within the breast. That is, upon movement of the foot 64 towards the distal end 48, the substance 40 is urged into the breast area in a direction 68 with a substantial directional component vector 120 (FIG. 6) that is normal to the panel member 78. Although FIG. 5 illustrates an applicator inserted at the periphery of the breast, it should be noted that an applicator of the present invention can also be inserted at the peri-aureolar area of the breast.

Figure 7:
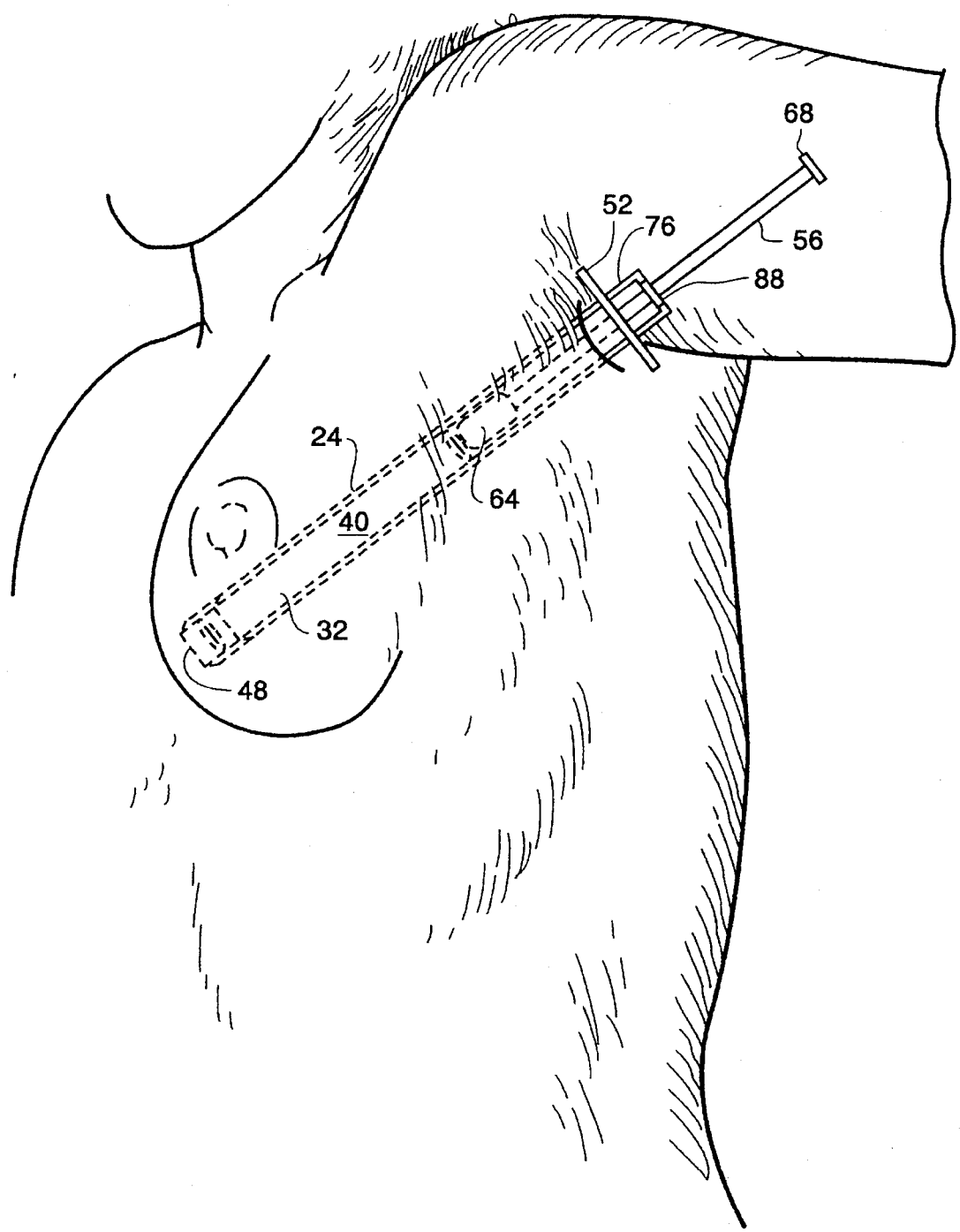
FIG. 7 illustrates the operation of the second embodiment of the applicator during the process of releasing the substance 40 from the housing chamber 32.

FIG. 7 illustrates an alternative method for using the present embodiment wherein the applicator has a substantially straight length and the path of insertion to a breast initiates substantially from the arm pit, although other peripheral sites could be utilized, such as the umbilical region or lateral abdomen. In this context, the applicator 20 may need to be longer than the applicator 20 used in FIG. 5. Further note that, in using the applicator 20 of FIG. 7, the chamber 32 may be filled with a substance 40 only a portion of its length from the distal end 48. Thus, by retracting the substance retaining assembly 76 only as far as the chamber 32 is filled with the substance 40, the substance 40 can be released substantially only into a breast area from a distance point of body entry.

Figure 8:
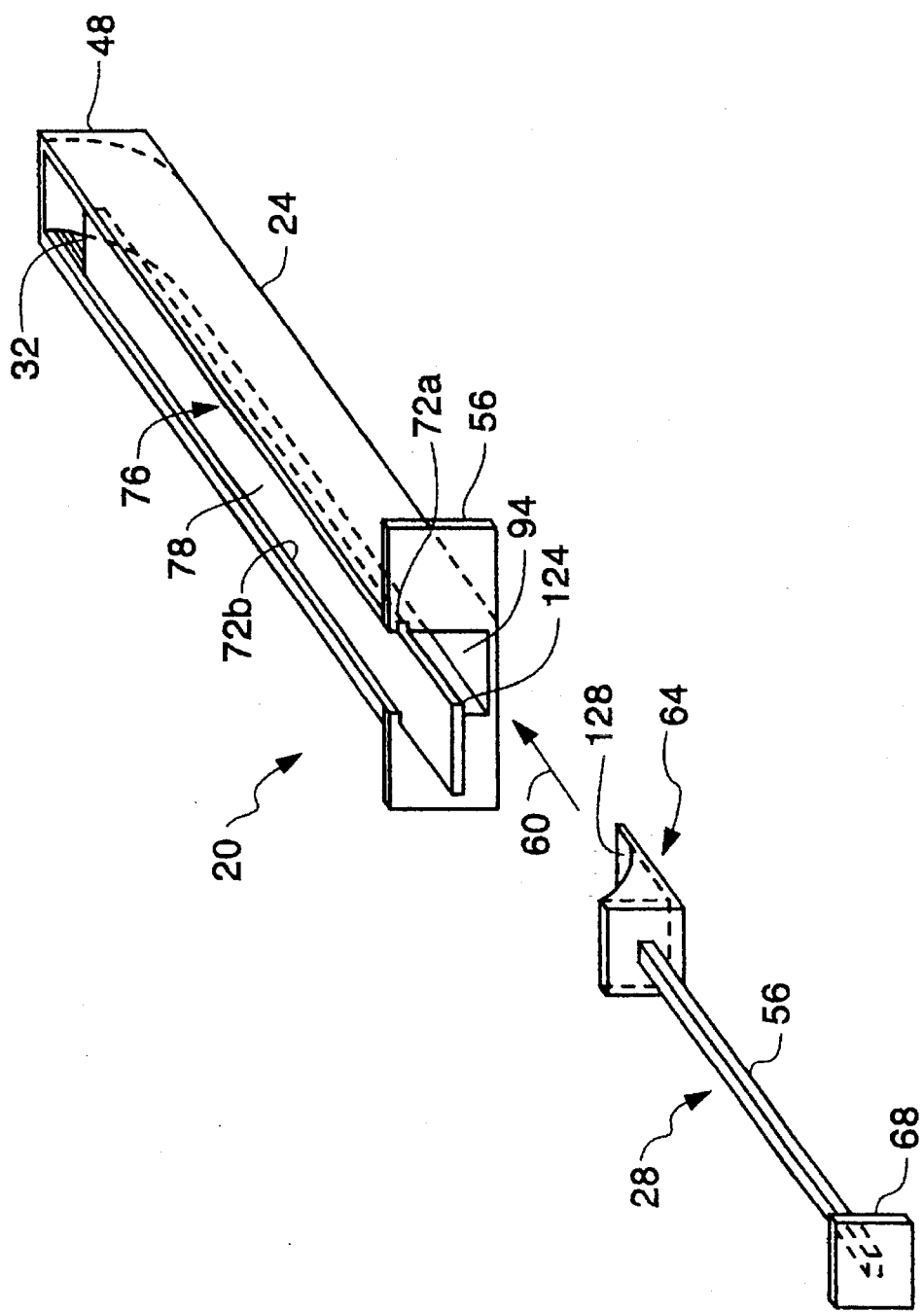
FIG. 8 presents a third embodiment of the present invention.

FIG. 8 presents yet another embodiment of the applicator 20. This embodiment is substantially similar to the previous two embodiments with the exception of the following noteworthy variations. The first variation relates to the tracks 72a and 72b, each of which is embodied by a slot facing toward the interior of the chamber 32. Thus, the substance retaining assembly 76 need not be provided with runners 82. Further, note that, in the present embodiment, the substance retaining assembly 76 is substantially contained within the housing 24 when the substance retaining assembly 76 is in a closed position abutting against the distal end 48. A second variation in this embodiment relates to the manner in which the substance retaining assembly 76 is retracted from the housing 24. That is, instead of a tab 88 as disclosed in the previous embodiment (FIG. 3), the present embodiment includes an extension 124 of the panel member 78 as the means for positioning or retracting the substance retaining assembly 76. Thus, in the fully closed position for the substance retaining assembly 76, the extension 124 protrudes sufficiently beyond the housing 24 such that it can be easily gripped for slidably moving the substance retaining assembly 76 within the tracks 72. A third variation with regard to the embodiment of FIG. 8 is the shape of the foot 64. That is, the foot 64 is configured substantially as a scoop or slidable ramp whereby the surface 128 which contacts the substance 40 to be released into a body area is concave. Thus, by filling the chamber 32 with a substance 40 and inserting the plunger 28 into the housing rear opening 94 as indicated by arrow 60, this embodiment of the applicator 20 can be used in a manner similar to the previous embodiment.

Note that the above embodiments, as well as other embodiments, may be used to insert a substance 40 into any number of body areas. That is, the invention is not limited to nasal and breast implants. Thus, as the various embodiments above illustrate, the length, the cross-sectional size, and the shape of the applicator 20 can vary to accommodate a particular insertion body area, insertion procedure and substance 40 to be inserted.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiment described hereinabove is further intended to explain the best mode presently known of practicing the invention and to enable others skilled in the art to utilize the invention as such, or other embodiments, and with the various modifications required by their particular application or uses of the invention. It is intended that the appended claims be construed to include alternative embodiments to the extent permitted by the prior art.

What is claimed is:

1. An applicator assembly for providing an insert substance in a body receiving area, comprising:

a housing having a length and a chamber running substantially the entire length of the housing, an opening in a side of said housing running substantially the length of the housing, means, running substantially the entire length of the housing, for restricting the side opening to the housing and for holding said substance within said chamber, said housing further having an open end with an opening and a distal end, a plunger, which is sized to be inserted into the housing end opening, including a shaft which extends substantially the length of the chamber, said plunger and said distal end together including means for urging the substance out the opening in the side of said housing as the plunger is advanced through the housing in the direction of the distal end.

2. An assembly, as claimed in claim 1, wherein:

said means for restricting and holding includes a retaining member removably joined to said housing and including a panel member that encloses a length of said chamber.

3. An assembly, as claimed in claim 2, wherein:

said retaining member is moved to permit said insert substance to move in a direction substantially perpendicular to said housing length.

4. An applicator assembly, as claimed in claim 2, wherein:

said retaining member is moved to permit said insert substance to move from said chamber under a force of gravity.

5. An assembly, as claimed in claim 2, wherein:

said panel member has a predetermined contour for following a path in the body receiving area.

6. An assembly, as claimed in claim 2, wherein: said retaining member is flexible.

7. An assembly, as claimed in claim 1, wherein:

said means for restricting and holding includes rail means fixedly connected to said housing side.

8. An assembly, as claimed in claim 1, wherein:

said distal end is closed to prevent movement of the insert substance from said housing chamber in a direction substantially parallel to said housing length.

9. An assembly, as claimed in claim 1, wherein:

the insert substance is suitable for contact with living tissue.

10. An assembly, as claimed in claim 1, wherein:

a cross-section of said housing traversing said length consists of one of an elliptical, oval, rectangular and round shape.

11. An assembly, as claimed in claim 1, wherein:

said housing includes a gripping wing that is connected adjacent to said open end and said gripping wing has a width that is greater than a width of remaining portions of said housing.

12. An assembly, as claimed in claim 2, wherein:

said retaining member includes a tab that extends at an angle relative to said panel member.

13. An assembly, as claimed in claim 12, wherein:

said housing includes a gripping wing having a height and said tab of said retaining member has a height greater than said gripping wing height.

14. An assembly, as claimed in claim 13, wherein:

said plunger includes a foot member for moving the insert substance from said chamber.

15. An assembly, as claimed in claim 14, wherein:

said plunger has a length at least greater than one-half a length of said chamber.

16. An assembly, as claimed in claim 1, wherein:

said housing conforms to a contour of the body receiving area.

17. An assembly, as claimed in claim 1, wherein:

said housing length is curved.

18. An assembly, as claimed in claim 1, wherein said housing is flexible.

* * * * *